(12) United States Patent
Xiao et al.

(10) Patent No.: US 7,803,542 B2
(45) Date of Patent: Sep. 28, 2010

(54) SIGNAL-ON ARCHITECTURE FOR ELECTRONIC, OLIGONUCLEOTIDE-BASED DETECTORS

(75) Inventors: Yi Xiao, Goleta, CA (US); Arica Lubin, Santa Barbara, CA (US); Kevin Plaxco, Santa Barbara, CA (US)

(73) Assignee: The Regents of the University of California, Oakland, CA (US)

( * ) Notice: Subject to any disclaimer, the term of this patent is extended or adjusted under 35 U.S.C. 154(b) by 680 days.

(21) Appl. No.: 11/564,674

(22) Filed: Nov. 29, 2006

(65) Prior Publication Data

US 2007/0154909 A1 Jul. 5, 2007

Related U.S. Application Data

(60) Provisional application No. 60/740,940, filed on Nov. 29, 2005.

(51) Int. Cl.
*C12Q 1/68* (2006.01)
*C12M 1/34* (2006.01)
(52) U.S. Cl. ........................... 435/6; 435/287.2
(58) Field of Classification Search .................. 435/6, 435/287.2
See application file for complete search history.

(56) References Cited

U.S. PATENT DOCUMENTS

| | | | |
|---|---|---|---|
| 4,840,893 A | 6/1989 | Hill et al. | |
| 5,139,812 A | 8/1992 | Lebacq | 427/7 |
| 5,312,728 A | 5/1994 | Lizardi et al. | |
| 5,942,388 A | 8/1999 | Willner et al. | |
| 6,221,586 B1 | 4/2001 | Barton et al. | |
| 6,264,825 B1 | 7/2001 | Blackburn et al. | |
| 6,350,580 B1 | 2/2002 | Sorge | |
| 6,451,588 B1 | 9/2002 | Egholm et al. | |
| 2001/0024788 A1 | 9/2001 | Hashimoto | |

(Continued)

FOREIGN PATENT DOCUMENTS

CN 1422960 6/2003

(Continued)

OTHER PUBLICATIONS

Drummond et al. Electrochemical DNA sensors. Nat Biotechnol 21:1192-1199 (2003).

(Continued)

*Primary Examiner*—Kenneth R. Horlick
(74) *Attorney, Agent, or Firm*—Carol L. Francis; Bozicevic, Field & Francis, LLP

(57) ABSTRACT

The invention provides a general "signal-on" architecture for oligonucleotide-based detectors that leads to order of magnitude increases in signal gain and sensitivity as compared to prior art detectors. The detectors of the invention rely on base pairing between two oligonucleotide strands, the sensor strand and the blocker strand. In the 'off' position of the detector, i.e., in the absence of target, the blocker strand and sensor strand are base-paired. As shown in FIG. 1, the formation of comparatively rigid, duplex DNA prevents the redox moiety from approaching the electrode surface, thereby suppressing Faradaic currents. When target is added to the system, the target displaces the blocker strand, binds to the sensor strand, liberating the end of the redox-labeled oligonucleotide to produce a flexible element. This, in turn, allows the redox moiety to collide with the electrode surface, producing a readily detectable Faradaic current.

31 Claims, 7 Drawing Sheets

U.S. PATENT DOCUMENTS

| | | |
|---|---|---|
| 2002/0006617 A1 | 1/2002 | Fan et al. |
| 2002/0012930 A1 | 1/2002 | Rothberg et al. |
| 2004/0101890 A1 | 5/2004 | Meade et al. |
| 2004/0191801 A1 | 9/2004 | Heeger et al. |
| 2004/0219523 A1 | 11/2004 | Stanton et al. |
| 2005/0112605 A1 | 5/2005 | Heeger et al. |
| 2005/0233358 A1 | 10/2005 | Thorp et al. |
| 2007/0020641 A1 | 1/2007 | Heeger et al. |

FOREIGN PATENT DOCUMENTS

| | | |
|---|---|---|
| CN | 1422961 | 6/2003 |
| WO | WO 99/57317 | 11/1999 |
| WO | WO 01/40511 | 6/2001 |
| WO | WO 01/40511 A2 | 6/2001 |
| WO | WO/2004/035929 | 4/2004 |
| WO | 2005036133 | 4/2005 |

OTHER PUBLICATIONS

Thorp et al. Cutting out the Middleman: DNA Biosensors Based on Electrochemical Oxidation. Trends Biotechnol 16:117-121 (1998).

Katz et al. Electroanalytical and Bioelectroanalytical Systems Based on Metal and Semiconductor Nanoparticles. J Electroanal 16:19-44 (2004).

Potyrailo et al. Adapting Selected Nucleic Acid Ligands (Aptamers) to Biosensors. Anal Chem 70:3419-3425 (1998).

Macaya et al. Structural and functional characterization of potent antithrombotic oligonucleotides possessing both quadruplex and duplex motifs. Biochemistry 34:4478-4492, (1995).

Padmanabhan,et al. An Ambiguous of A DNA 15-mer Thrombin Complex. Acta Crystallogr. D52:272-282 (1996).

Immoos et al., Conformationally gated electrochemical gene detection.ChemBioChem 5:1100-1103 (2004).

Du, H., et al. Hybridization-based unquenching of DNA hairpins on Au surfaces: prototypical "Molecular Beacon" biosensors. J Am Chem Soc. 2003, vol. 125, pp. 4012-4013.

Kuhr, et al. "Electrochemical DNA analysis comes of age" *Nature Biotech* 18:1042-1043 (2000).

Willner, Itamer "Biomaterials for Sensors, Fuel Cells, and Circuitry" *Science* 298:2407-2408 (2002).

Fritz, et al. "Electronic detection of DNA by its intrinsic molecular charge" *Proc. Natl. Acad. Sci., USA* 99(22):4142-14146 (2002).

Brazill, et al. "Capillary Gel Electrophoresis with Sinusoidal Voltammetric Detection: A Stratego To Allow Four-"Color" DNA Sequencing" *Anal Chem.* 73:4882-4890 (2001).

Palecek, et al. "Electrochemistry of Nucleic Acids and Development of DNA Sensors" *Crit. Rev. Anal. Chem.* 32(3):261-270 (2002).

Millan et al."Sequence-Selective Biosensor for DNA Based on Electroactive Hybridization Indicators" *Anal. Chem.* 65:2317-2323 (1993).

Kelley, et al. "Single-base mismatch detection based on charge transduction through DNA" *Nucleic Acids Res*.27(24):4830-4837 (1999).

Ihara et al "Ferrocene-oligonucleotide conjugates fro electrochemical probing of DNA" *Nucleic Acids Res.* 24(21):4273-4280 (1996).

Yu, et al. Electronic Detection of Single-Base Mismatches in DNA with Ferrocene-Modified Probes: *J. Am. Chem. Soc.* 123:11155-11161 (2001).

Umek et al. "Electronic Detection of Nucleic Acids" *J. Mol. Diag.* 3(2):74-84 (2001).

Park et al. "Array-Based Electrical Detection of DNA with Nanoparticle Probes" *Science* 295:1503-1506 (2002).

Korri-Youssoufi, et al. "Toward Bioelectronics: Specific DNA Recognition Based on an Oligonucleotide-Functionalized Polypyrrole" *J. Am. Chem. Soc.* 119:7388-7389 (1997).

Clelland et al. "Hiding messages in DNA microdots" *Nature* 399:533-534 (1999).

Cox et al. "Bar coding objects with DNA" *Analyst* 126:545-547 (2001).

Fan et al. "Spectroscopy and Electrochemistry of the Covalent Pyridine-Cytochrome c Comples and a Pyridine-Induced, "Alkaline-like" Conformation" *J. Phys. Chem. I(B)* 106:11375-11383 (2002).

Hirst, J. et al. "Kinetics and Mechanism of Redox-Coupled, Long-Range Proton Transfer in an Iron-Sulfur Protein. Investigation by Fast-Scan Protein-Film Voltammetry" *J. Am. Chem. Soc.* 120:7085-7094 (1998).

Tyagi et al. "Molecular Beacons: Probes that Fluoresce upon Hybridization" *Nat. Biotechnol.* 14:303-308 (1996).

Boon et al. "An electrical probe of protein-DNA interactions on DNA-modified surfaces" *Nat. Biotechnol.* (2002).

O'Sullivan, et al. "Aptasensors—the future of biosensing?" *Anal. Bioanal. Chem.* 372:44-48 (2002).

Robertson et al. "In vitro selection of an allosteric ribozyme that transduces analytes to amplicons" *Nature Biotech* 17:62-66 (1999).

Stojanovic et al. "Fluorescent Sensors Based on Aptamer Self-Assembly" *J. Am. Chem. Soc.* 122:11547-11548 (2000).

Cook et al. Methylated DNA labels for marking objects: *Biotechnol. Lett* 25:89-94 (2003).

Immoos et al. "Characterization of Immobilized DNA Hairpins Containing Tethered Redox Probes" *Dept. of Chemistry, Duke University, P.M. Gross Laboratory*, Durham, NC, (2002).

Bock et al. "Selection of single-stranded DNA molecules that bind and inhibit human thrombin" *Nature* 355:564-566 (1992).

Bowtell, D.D.L. "Options available-from start to finish-for obtaining expression data by microarray" *Nat. Genet.* 21:25-32 (1999).

Brazill et al. "Sinusoidal voltammetry: a frequency based electrochemical detection technique" *J. Electroanal Chem.* 531:119-132 (2002).

Buijsman et al. "Design and Synthesis of a Possible Mimic of a Thrombin-Binding DNA Aptamer" *Bioorg. & Med. Chem. Lett* 7(15):2027-2032 (1997).

Cheng et al. "Chip PCR. II. Investigation of different PCR amplification systems in microfabricated silicon-glass chips" *Nuc. Acid. Res.* 24(2):380-385 (1996).

Cheng et al. "Preparation and hybridization analysis of DNA/RNA from *E. coli* on microfabricated bioelectronic chips" *Nat. Biotech.* 16:541-546 (1998).

Cox et al. "Automated Acquisition of Aptamer Sequences" *Comb. Chem. & High Throughput Screening* 5:289-299 (2002).

Dittmer et al. "A DNA-Based Machine That Can Cyclically Bind and Release Thrombin" *Agnew. Chem. Int. Ed.* 43:3550-3553 (2004).

Ellington et al. "In vitro selection of RNA molecules that bind specific ligands" *Nature* 346:818-822 (1990).

Fan et al. "Electrochemical Interrogation of conformational changes as a reagentless method for the sequence-specific detection of DNA" *Proc. Natl. Acad. Sci. USA* 100(16):9134-9137 (2003).

Fang et al. "Molecular Beacons" *Cell. Biochem. Biophys.* 37:71-81 (2002).

Fang et al. "Synthetic DNA Aptamers to Detect Protein Molecular Variants in a High-Throughput Fluorescence Quenching Assay" *Chem Bio Chem* 4:829-834 (2003).

Fukusho et al. "In vitro selection and evaluation of ma aptamers that recognize arginine-rich-motif model peptide on a quartz-crystal microbalance" *Chem. Commun.* 1:88-89 (2002).

Hamaguchi et al. "Aptamer Beacons for the Direct Detection of Proteins" *Anal. Biochem.* 294:126-131 (2001).

Heme et al. "Characterization of DNA Probes Immobilized on Gold Surfaces" *J. Am. Chem. Soc.* 119:8916-8920 (1997).

Hianik et al. "Detection of aptamer-protein interactions using QCM and electrochemical indicator methods" *Bioorg. & Med. Chem. Lett.* 15:291-295 (2005).

Hianik et al. "The study of the binding of globular proteins to DNA using mass detection and electrochemical Indicator methods" *J. Electroanal Chem* 564:19-24 (2004).

Ho et al. "Optical Sensors Based on Hybrid Aptamer/Conjugated Polymer Complexes" *J. Am. Chem. Soc.* 126:1384-1387 (2004).

Iqbal et al. "A review of molecular recognition technologies for detection of biological threat agents" *Biosens. & Bioelectron* 15:549-578 (2000).

Kankia et al. Folding of the Thrombin Aptamer into a G-Quadruplex with $Sr^{2+}$: Stability, Heat, and Hydration *J. Am. Chem. Soc.* 123:10799-10804 (2001).

Lee et al. "A Fiber-Optic Microarray Biosensor Using Aptamers as Receptors" *Anal. Biochem.* 282:142-146 (2000).

Leopold et al. "Influence of Gold Topography on Carboxylic Acid Terminated Self-Assembled Monolayers" *Langmuir* 18:978-980 (2002).

Li et al. "Molecular Adtamer Beacons for Real-Time Protein Recognition" *Biochem. & Biophys. Res. Commun.* 292:31-40 (2002).

Li et al. "Real-time Protein Monitoring Based on Molecular Beacons" *Curr. Proteomics* 1:315-324 (2004).

Liss et al. "An Aptamer-Based Quartz Crystal Protein Biosensor" *Anal. Chem.* 74(17):4488-4495 (2002).

Macaya et al. "Thrombin-binding DNA aptamer forms a unimolecular quadruplex structure in solution" *Proc. Natl. Acad. Sci. USA* 90:3745-3749 (1993).

Minunni et al. "Development of biosensors with aptamers as bio-recognition element: the case of HIV-1 Tat protein" *Biosens.& Bioelectron.* 20:1149-1156 (2004).

O'Connor et al. "A Nemstian electron source model for the ac voltammetric response of a reversible surface redox reation using large-amplitude ac voltages" *J. Electroanal. Chem.* 466:197-202 (1999).

Padmanabhan et al. "The Structure of α-Thrombin Inhibited by a 15-Mer Singl-stranded DNA Aptamer" *Biol. Chem.* 268(24):17651-17654 (1993).

Pavlov et al. "Aptamer-Functionalized Au Nanoparticles for the Amplified Optical Detection of Thrombin" *J. Am. Chem. Soc.* 126:11768-11769 (2004).

Rajendran et al. "In vitro selection of molecular beacons" *Nucleic Acids. Res.* 31(19):5700-5713 (2003).

Robertson et al. "Selection in vitro of an RNA enzyme that specifically cleaves single-stranded DNA" *Nature* 344:467-469 (1990).

Savran et al. "Micromechanical Detection of Proteins Using Aptamer-Based Receptor Molecules" *Anal. Chem.* 76:3194-3198 (2004).

Smirnov et al. "Effect of Loop Sequence and Size on DNA Aptamer Stability" *Biochemistry* 39:1462-1468 (2000).

Stojanovic et al. "Aptamer-Based Folding Fluorescent Sensor for Cocaine" *J. Am. Chem. Soc.* 123:4928-4931 (2001).

Tan et al. "Molecular beacons" *Curr. Opin. Chem. Biol.* 8:547-553 (2004).

Tombelli et al. "New Trends in Nucleic Acids Based Biosensors" *Anal. Lett.* 37(6)1037-1052 (2004).

Wang et al. "A DNA Aptamer Which Binds to and Inhibits Thrombin Exhibits a New Structural Motif for DNA" *Biochemistry* 32:1899-1904 (1993).

Willner, Itamar "Biomaterials for Sensors, Fuel Cells, and Circuitry" *Science* 298:2407-2408 (2002).

Winzeler et al. "Fluorescence-Based Expression Monitoring Using Microarrays" *Methods. Enzymol.* 306:3-18 (1999).

Yamamoto et al. "Molecular beacon aptamer fluoresces in the presence of Tat protein of HIV-1" *Genes Cells* 5:389-396 (2000).

SIGNAL-ON ARCHITECTURE FOR ELECTRONIC, OLIGONUCLEOTIDE-BASED DETECTORS

CROSS-REFERENCE TO RELATED PATENT APPLICATIONS

This application claims the benefit of U.S. provisional application Ser. No. 60/740,940, filed 29 Nov. 2005, the disclosure of which is incorporated herein by reference in its entirety.

REFERENCE TO GOVERNMENT SUPPORT

The U.S. Government has a paid-up license in this invention and the right in limited circumstances to require the patent owner to license others on reasonable terms as provided by Grant No. NSF-DMR-0099843 awarded by the National Science Foundation; by Grant DAAD 19-03-D-004 awarded by the Institute for Collaborative Biotechnologies, U.S. Army Research Office; and by Grant No. NIH EB002046 awarded by the National Institutes of Health.

INTRODUCTION

A. Field of the Invention

This invention relates to bioelectronic detectors based on oligonucleotides (which term is defined to include synthetic and naturally-occurring nucleotide polymers such as aptamers, DNA, RNA, and the like as well as analogs thereof) and their use to detect molecular targets via target-induced strand displacement.

B. Background

A wide range of electronic DNA detection schemes have been described (reviewed in Drummond et al. *Nat Biotechnol* 21:1192-1199 (2003), Thorp et al. *Trends Biotechnol* 16:117-121 (1998) and Katz et al. *J Electroanal* 16:19-44 (2004)). Among promising recent examples are approaches based on conductive links produced through the catalytic deposition of silver by nanoparticle-linked secondary probes (Potyrailo, et al. *Anal Chem* 70:3419-3425 (1998)), the electrocatalytic oxidation of modified bases by $OS(bpy)_3^{3+}$ (Stojanovic et al. *J. Am. Chem. Soc.* 123:4928-4931 (2001)), the electrochemistry of water-soluble, ferrocene-functionalized cationic polythiophenes (Yamamoto, et al. *Genes Cells* 5:389-396 (2000)), ferrocene-linked triblock copolymer-DNA hybrids (Savran, et al. *Anal. Chem.* 76:3194-3198 (2004)) the electron transfer of ferrocenyl-tethered poly(amido-amine)dendrimer in a sandwich-type enzyme-linked DNA sensor (Fang, et al. *ChemBioChem* 4:829-834 (2003)), charge transport from electroactive DNA intercalators (with magnetic sample concentration) (Hamaguchi, et al. *Anal. Biochem.* 294:126-131 (2001); Dittmer, et al. *Agnew Chem. Int. Ed.* 43:3550-3553 (2004)), chronopotentiometric detection of micrometelong indium rod traer in a DNA sandwich hybridization assay (with magnetic sample concentration) (Bock et al. *Nature*, 355: 564-566 (1992); Macaya, et al. *Biochemistry* 34:4478-4492 (1995); and Padmanabhan, et al. *Acta Crystallogr*. D52: 272-282 (1996)) and anodic stripping voltammetry of silver nanoparticles deposited in a multistep reduction process initiated by a labeled secondary probe (Ho et al., *J. Am. Chem. Soc.* 126:1384-1387 (2004)).

Although the detection limits of the above-described sensor technologies often are impressive, achieving them requires the addition of exogenous, label-containing secondary probes and, typically, complicated, multicomponent deposition/amplification steps. For example, although Hwang et al. report an exceptional 0.1 fM detection limit, achieving it required a five-step assay including an enzyme-linked secondary probe, enzymatic reduction of p-aminophenyl phosphate, the concomitant reductive deposition of silver and, finally, anodic stripping voltammetry to quantify the deposited silver. In contrast to these relatives cumbersome assays, the present invention provides a reagentless, single-step electrochemical oligonucleotide-based detection method, based target-induced strand displacement mechanism to achieve exceptional levels of detection of nucleic acids, as well as proteins and other biologic and non-biologic molecules of interest.

A related system involving an electroactive redox-tagged DNA stem-loop structure that self-assembles onto a gold surface via a gold-thiol bond is described in Fan et al. (*Proc. Nat'l Acad. Sci. USA* 100:9134-9137 (2003)). In the described system, hybridization induces a large conformational change in this surface-confined DNA structure, which in turn significantly alters the electron-transfer tunneling distance between the redox moiety and the electrode. One drawback of the signal-off architecture of this system is that it is more susceptible to false positives arising from the degradation of the sensor elements and the gain of such a signal-off detector is limited; at best the suppressed response can only be 100% of the original signal intensity.

These problems would be alleviated by a "signal-on" mechanism that, instead, produces significant increases in peak current upon target recognition. In contrast to signal-off architectures, signal-on detectors do not exhibit an inherent limitat on signal intensity. Indeed, under ideal conditions (as the detector background signal approaches zero), the detector gain increases without limit; thus the signal sensitivity of such detectors is often significantly improved over that of signal-off architectures. Recently, one group reported a signal-on, "two-piece" electrochemical assay for DNA detection with a 200 pM detection limit (Immoos et al., *ChemBioChem* 5:1100-1103 (2004)). This detector, however, requires the fabrication of a synthetically complex-ferrocene-labeled DNA-poly(ethylene glycol) triblock macromolecule that binds a target DNA strand. The present invention provides an oligonucleotide-based detector that is signal-on, easily assembled and exhibits enhanced gain, ease of use and improved detection limits as compared to existing DNA detectors.

SUMMARY OF THE INVENTION

One aspect of the invention provides detectors for assessing the presence of a molecular target comprising: a) an oligonucleotide blocker; b) an oligonucleotide sensor having a first region complementary to a first region of the blocker, which first regions are capable of forming a first double-stranded complex, and wherein the sensor is capable of specifically interacting with the molecular target thereby disrupting the first double-stranded complex; and c) an electrode capable of detecting redox signals from a redox moiety covalently attached to either the blocker or the sensor, wherein at least one of the sensor and the blocker is covalently attached to the electrode. When the first double-stranded complex is formed, the redox moiety is in a first state relative to the electrode, and when the first double-stranded complex is disrupted by the molecular target, the redox moiety is in a second state relative to the electrode, wherein the first and second states give rise to distinguishable redox signals detectable by the electrode. Preferably, the redox signal detectable in the second state is greater than the redox signal in the first state. The increase is detectable signal can be achieved by the redox moiety being capable of being closer to the electrode in the second state as compared to the first state. The redox label may be physically moved closer to the electrode upon binding of the target. Alternatively, the redox label may become more flexible, allowing it to diffuse or otherwise move towards the electrode. The redox moiety can covalently attached to the blocker or to the sensor. Optionally, more than one redox moiety is attached to either the blocker or the sensor. The sensor, the blocker or both is attached to the electrode. In one implementation, the sensor and blocker are directly or indirectly attached to one another. However, the attachment is not via a continuous backbone shared by the sensor and blocker. In other words, the sensor and blocker do not form a single oligonucleotide strand. The electrode can be a metallic conductor, a non-metallic conductor, a metallic semiconductor and a non-metallic semiconductor. Preferably, the electrode comprises a metal, such as gold. The redox moiety can be selected from purely organic redox moieties and derivatives thereof, organo-metallic redox moieties and derivatives thereof, and biological redox moieties and derivatives thereof.

Another aspect of the invention provides methods for assessing the presence of a molecular target in a sample comprising the steps of (a) contacting the sample with a detector of the invention and (b) sensing a first redox signal with the detector, wherein the first redox signal is indicative of the presence of the molecular target in the sample. In certain implementations, the methods can further comprise the steps of (c) contacting a standard with the detector; (d) sensing a second redox signal with the detector; and (e) comparing the first redox signal to the second redox signal. In a preferred implementation, the standard contains a known amount of the molecular target and comparing the first redox signal to the second redox signal comprises correlating a similarity in the first and second redox signals with a similar level of the molecular target in the sample and the standard. Preferably, the standard contains no molecular target and comparing the first redox signal to the second redox signal comprises correlating a similarity in the first and second redox signals with an absence of molecular target in the sample and a difference in the first and second redox signals with the presence of the molecular target in the sample.

BRIEF DESCRIPTION OF THE DRAWINGS

FIG. 10A provides alternating current voltammograms of the sensor obtained after incubation at various $Pb^{2+}$ concentrations. FIG. 10B provides a dose-response curve for the lead sensor graphically illustrating that the dynamic range of this sensor covers target concentrations which range from 1 nM to 10 nM. The illustrated error bars represent the standard deviation of 4 measurements conducted with a single electrode at each concentration.

FIG. 14A demonstrates that little signal change is observed when this implementation of the sensor (directed against $Pb^2)^+$ is challenged with divalent metal ions other than $Pb^{2+}$ (all at 10 μM). FIG. 14 B graphically illustrates the signals obtained after the sensor is challenged with positive control samples comprised of lead at 120 or 80 ppm in buffer, with extracts of soil spiked with equivalent amounts of lead, and extracts from a control soil sample lacking detectable lead. All five samples were extracted with acetic acid (to solubilize the lead) using EPA Method 3050B and diluted 100-fold with buffer prior to analysis (i.e. whereas the initial lead concentrations were 120 and 80 ppm, the detected levels were 1200 and 800 ppb).

DETAILED DESCRIPTION

A. Overview

Figure 1:
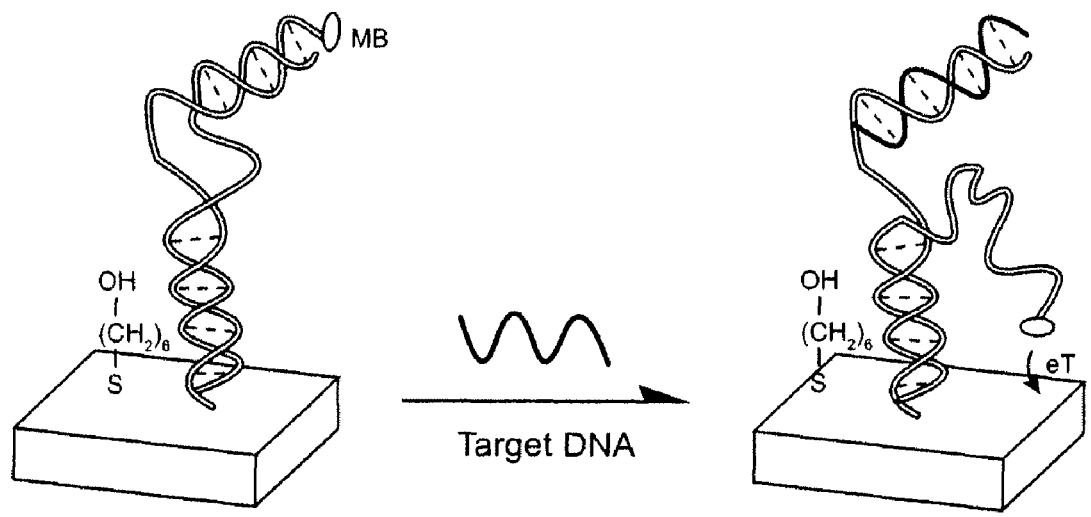
FIG. 1 provides a schematic diagram (scheme A) of the mechanism of action of one implementation of a signal-on electrochemical detector based on the conformational change of the redox-labeled duplex DNA via target-induced strand displacement.

The invention provides a general "signal-on" architecture for oligonucleotide-based detectors that leads to order of magnitude increases in signal gain and sensitivity as compared to prior art detectors. The detectors of the invention rely on base pairing between two oligonucleotide strands, the sensor strand and the blocker strand. In the 'off' position of the detector, i.e., in the absence of target, the blocker strand and sensor strand are base-paired. As shown in FIG. 1, the formation of comparatively rigid, duplex DNA prevents the redox moiety from approaching the electrode surface, thereby suppressing Faradaic currents. When target is added to the system, the target displaces the blocker strand, binds to the sensor strand, liberating the end of the redox-labeled oligonucleotide to produce a flexible element. This, in turn, allows the redox moiety to collide with the electrode surface, producing a readily detectable Faradaic current.

It will be appreciated that this oligonucleotide is representative of oligonucleotides generally (including DNA, RNA, aptamers, ribozymes, DNAzymes and non-natural nucleic acid analogs of all of the preceding) and that the redox moiety is representative of redox moieties generally and that the change in state of the redox moiety which leads to the "signal-on" event may be a change (shortening) in distance between the redox moiety and the electrode but also may be considered more generally as any static or dynamic change in which the environment of the redox moiety which would lead to enhanced electron transfer between the redox moiety and the electrode.

It will also be appreciated that there are several variations of this invention which provide similar results. In the embodiment just mentioned, the redox moiety is provided on the blocker oligonucleotide which hybridizes with the electrode-linked sensor oligonucleotide. Alternatively, the redox moiety could be on the sensor with the blocker merely forming the rigid, target-binding structure with it, which the target disrupts. Similarly, in the embodiment just mentioned, it is the sensor which is coupled to the electrode. Alternatively, both the sensor and the second oligonucleotide could be coupled to the electrode or they could be coupled to one another with one of them coupled to the electrode, just as long as a structure is provided in which the target can interact with the rigid duplex DNA and disrupt it by displacing one of the duplex members such that the redox moiety is able to provide the "signal-on" signal.

In yet another implementation (FIG. 2), the blocker is attached to both the redox moiety and the electrode. In the initial "off" position, the sensor strand forms a rigid duplex with the blocker. When the target is added to the detector, the redox moiety-labeled blocker is displaced from the sensor, releasing the flexible single-strand turning 'on' the detector. Because the sensor and target form a duplex, one will appreciate that this implementation is not strictly reuseable and reagentless. However, the detector can easily be recharged by addition of fresh sensor oligonucleotide. The detector, optionally, can be stripped of any remaining sensor oligonucleotide under high salt, high temperature, or other high stringency conditions, prior to recharging with fresh sensor. The new sensor can be the same of different than the original sensor oligonucleotide. In yet another implementation, the sensor comprises a catalytically active polymer with nuclease activity (FIG. 3). Preferably, the nuclease is sequence specific or requires the presence of an ion or other cofactor to function. More preferably, the nuclease is a cofactor-requiring DNAzyme or ribozyme. The sensor is attached to both the redox moiety and the electrode. In the initial "off" position, the sensor strand forms a rigid duplex with the substrate nucleic acid (the blocker). When the target metal ion or cofactor is added to the detector, the substrate is cleaved by the catalytically active sensor. The two halves of the cleaved substrate dissociate from the sensor, releasing the flexible single-strand, thereby turning 'on' the detector. The detector can easily be recharged by addition of new substrate-blocker oligonucleotide.

B. Definitions

As defined herein, a "target" refers to refers to any ion, small organic molecule, oligonucleotide, protein, or other molecule, or a cell, virus or any other target that binds to a specific oligonucleotide sensor of the invention thereby disrupting an existing duplex with the blocker via either displacement or via catalytic cleavage. Exemplary targets that can interact with the oligonucleotide sensor include, but are not limited to, proteins (including specific post-translational modification of certain proteins and specific three-dimensional conformations of certain proteins), peptides, glycoproteins, hormones, receptors, antibodies, growth factors, nucleic acids, nucleotides, oligosaccharides, carbohydrates, transition state analogs, cofactors, viruses, nutrients, metabolites, drugs, toxins, biohazards, etc. In a preferred implementation, the target is an oligonucleotide having a sequence to which the oligonucleotide sensor is designed to hybridize.

The term "oligonucleotide," as used herein, refers to any polymer of nucleotides, nucleosides or nucleobases that is capable of forming double-stranded complexes through hydrogen bonds between nucleobases. Oligonucleotides include, but are not limited to, DNA, RNA, modified or synthetic DNA or RNA (including but not limited to nucleic acids comprising synthetic and naturally-occurring base analogs, or other sugars, and thiols). Other exemplary oligonucleotides include degradation-resistant polynucleoside amides, peptide nucleic acids (PNAs) and other nucleobase-containing polymers. A common PNA has a backbone consisting of repeating N-(2-aminoethyl) glycine unit, linked by amide bonds. Unlike DNA or RNA, PNA often does not contain any sugar or phosphate groups. The term "oligonucleotide" in no way defines or limits the length of the nucleic acids that may be used to practice the invention.

In a preferred implementation, the invention can also employ aptamers, which term describes a specific subset of oligonucleotides selected or designed for specific binding purposes. Aptamers, which are included within the class of "oligonucleotides" employed in the practice of the present invention are short oligonucleotides selected in vitro for specific, high-affinity binding to a broad range of molecular targets, are considered promising recognition elements for biodetector applications, as illustrated by a recent report of 10 pM thrombin detection using an aptamer-directed rolling-circle amplification assay. The aptamer-based detector architecture of the invention is sensitive and selective enough to work directly in blood and other complex, contaminant-ridden materials and, in contrast to other promising approaches, do not require processing steps or the addition of any exogenous reagents.

The term "nucleobase" refers to the mono- or bicyclic structures that connect two oligonucleotides via hydrogen bonds. Typically a nucleobase is a purine or pyrimidine derivative. Nucleobases include the standard DNA and RNA bases, adenosine, guanine, cytosine, thymine and uracil as well as other bases, such as, inosine, 5-methylcytosine, and 7-deazaguanosine. Typically, purines are complementary with pyrimidines. Pyrimidine-pyrimidine pairings generally are energetically unfavorable because the molecules are too far apart for hydrogen bonding to be established; purine-purine pairings generally are energetically unfavorable because the molecules are too close, leading to electrostatic repulsion. Nucleobases can form base pairs according to the canonical Watson-Crick base pairing: guanine (G) forming a base pair with cytosine (C); adenine (A) forming a base pair with thymine (T) in DNA and uracil (U) in RNA. In the context of the present invention, nucleobases may also form non-Watson-Crick base pairing with alternate hydrogen bonding patterns, such as Hoogsteen base pairs in which the N7 position of the purine base (as a hydrogen bond acceptor) and C6 amino group (as a donor), which bind the (N3-N4) face of the pyrimidine base.

C. Detector

The signal-on detector of the invention requires that the redox moiety-labeled oligonucleotide remains physically associated with the electrode after target binding so that the redox moiety can make contact with the electrode. In one implementation, the oligonucleotide having the redox moiety is directly attached to the electrode. In another implementation, the labeled oligonucleotide is indirectly attached to the electrode. For example, the unlabeled oligonucleotide can be attached to the electrode. The sensor and blocker oligonucleotides then share two regions of complementarity, one disruptable by target, the second unaffected by target (see FIG. 1). In an exemplary embodiment, a 12-base duplex, unaffected by the present of target has proven to be stable for 24 hours in simple buffers at room temperature under air. Alternatively, fully covalent systems in which the sensor and blocker strands are covalently linked to one another or both are linked to the electrode could demonstrate significantly improved stability and versatility.

Figure 2:
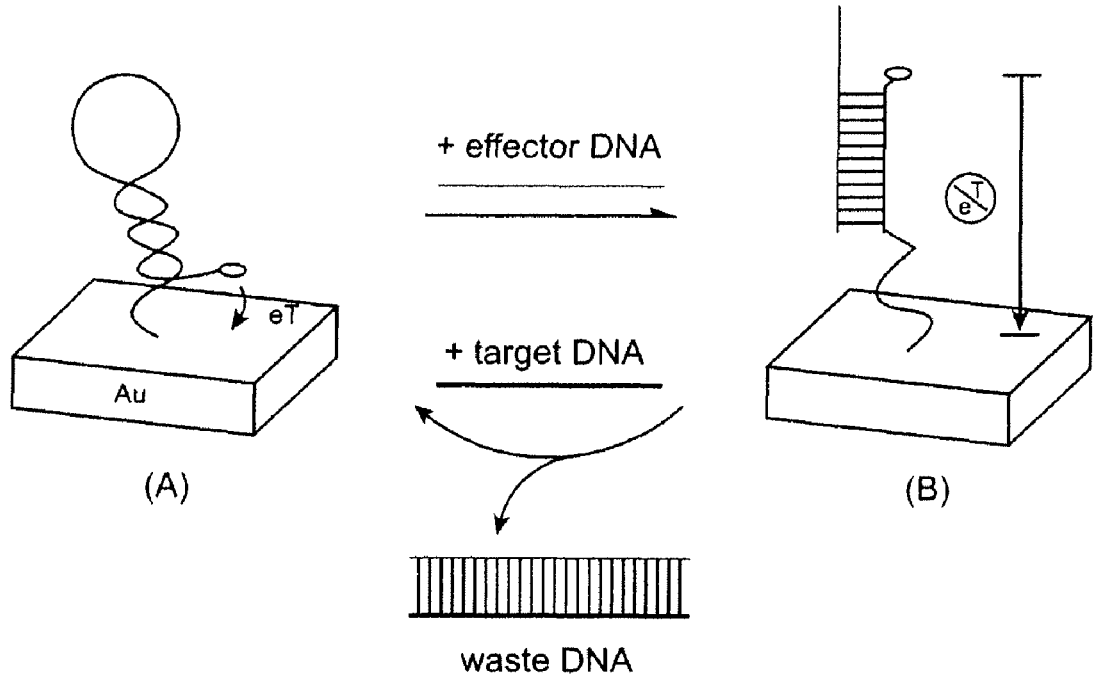
FIG. 2 provides a schematic diagram (scheme B) of the mechanism of action of another implementation of a signal-on electrochemical detector based on the conformational change of the redox labeled stem-loop DNA when exposing the detector to complementary sensor DNA (b), and then target DNA, (a).
Figure 3:
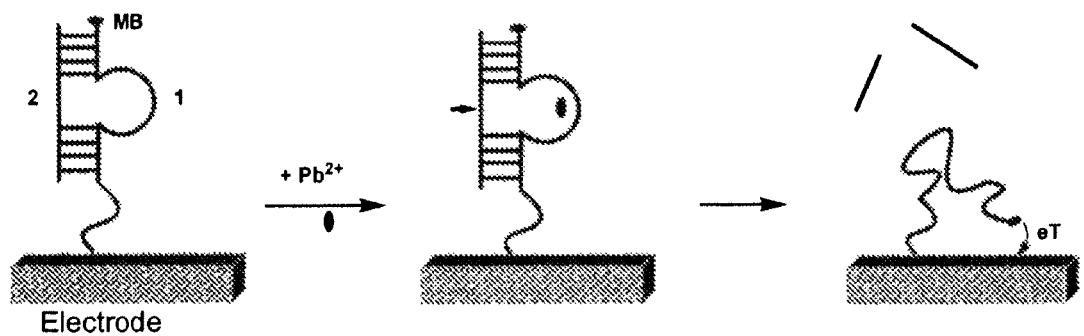
FIG. 3 provides a schematic diagram (scheme C) of the mechanism of action of an implementation of a signal-on electrochemical detector based on a conformational change in a redox-labeled duplex DNA via target-induced cleavage of a substrate (blocker) strand and subsequent displacement of the substrate fragments via a DNAzyme sequence (the sensor strand) that becomes catalytic upon target binding.

An alternative signal-on detector architecture, illustrated in FIG. 2, utilizes an immobilized single stranded, redox-labeled oligonucleotide that self hybridizes to form a stem-loop structure on an electrode. The hybridized stem-loop DNA probe brings the MB label in close proximity to the electrode surface, allowing the attached redox moiety to collide with (or weakly bind to) the electrode and transfer an electron. When the electrode-bound oligonucleotide hybridizes to a second complementary sensor oligonucleotide, formation of rigid duplex nucleic acid will force the MB redox moiety away from the electrode surface upon hybridization, thus impeding electron transfer from the redox moiety and producing only a minimal amount of Faradaic current. In the next step, target is added. Preferably, the target oligonucleotide is fully complementary to and hybridizes with the sensor. In certain implementations, the sensor oligonucleotide has a 'dangling' end that is complementary to the target but not he blocker. This dangling end can nucleate hybridization between the target and the sensor, starting at the dangling-end progressing to the entire length of the sensor. This process will lead to a displacement of the sensor oligonucleotide from the immobilized blocker oligonucleotide, the formation of sensor:target duplex in solution and the reformation of stem-loop structure in the immobilized redox-labeled oligonucletoide on the surface. Thus target recognition results in the redox moiety colliding with the electrode surface, thus generating an electrochemical signal.

Figure 4:
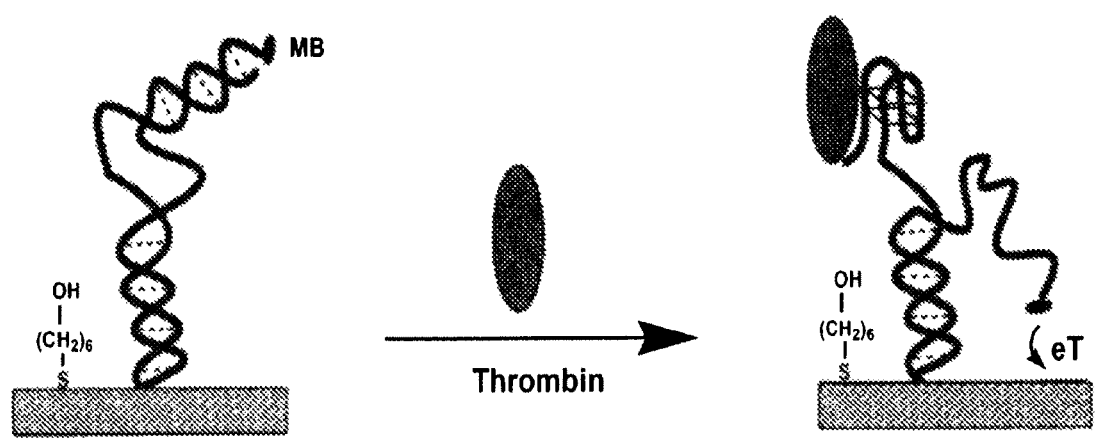
FIG. 4 provides a schematic diagram (scheme D) illustrating the mechanism of another implementation of a signal-on electronic, aptamer-based detector. Thrombin, as a representative target, induces stand displacement and stabilizes the alternative, target-binding conformation of the aptamer (for this example, a G-quadruplex structure) liberating the a redox-labeled oligonucleotide to produce a flexible, single-stranded DNA element.

This "signal-on" detector generates a greater signal response upon target recognition than previously observed for the signal-off E-DNA detector (Fan, C., Plaxco, K. W. and Heeger, A. J. (2003) "Electrochemical interrogation of conformational changes as a reagentless method for the sequence-specific detection of DNA." *Proc. Natl. Acad. Sci. USA*, 100, 9134-9137). Experimental results show that challenging the detector with 4 nM of target produces a 38% increase in signal upon target recognition. When the concentration of target was increased to 11.7 nM, a 129% increase in electrochemical signal was observed. And at 400 nM target concentration, the signal change appears to reach a saturation platform with a 500% increase of signal. Given these results, the dynamic range of this configuration of the detector covers target concentrations ranging from 4 nM to 400 nM. The estimated detection limit for the signal-on architecture is 2 nM. Control experiment indicates that addition of random, non-complementary DNA sequence has no change on the current response. While large signal changes were observed with target concentrations of 4 nM and above, it is believed that the much greater sensitivity can be achieved utilizing the signal-on detectors of the invention. For example, the immobilized blocker:sensor duplex still gives a significant background signal in the absence of target. This background signal may simply be due to the equilibrium between the duplex and the stem-loop structured redox-labeled blocker. Such background signal can be decreased by destabilizing the stem-loop structure or by increasing the stability of the sensor:blocker duplex. Similarly, other architectures may be utilized, as illustrated in FIGS. 1, 3 and 4. The background signal can also be reduced by using alternating current voltammetric or other electrochemical measurements at a frequency that supports electron transfer from the stem-loop more efficiently than it supports electron transfer from the off conformation.

In one implementation, a signal-on detector is constructed by covalently attaching a thiolated oligonucleotide aptamer to an electrode (FIG. 4). A redox-labeled, partially complementary oligonucleotide blocker is added and forms a double stranded complex with the electrode-bound aptamer. While not being limited to a theory of the invention, it is believed that the binding-competent conformer is in equilibrium with the double stranded conformation. Because the molecular target only binds the non-duplex oligonucleotide, target binding drives the equilibrium from duplex structure toward, for example, the corresponding aptameric G-quadruplex liberating the end of the redox moiety-labeled oligonucleotide as a flexible element and thus producing a detectable electronic signal as shown in FIG. 4.

The signal-on detector architecture described is applicable to almost any aptamer. There are, for example, reports in the scientific literature describing successful efforts to rationally engineer normally well-folded aptamers into optical aptamer beacons (aptamers that undergo a large scale conformational change in the presence of their target) by adding a short sequence to the 5' end which is complementary to the 3' end of the aptamer or a short sequence to either termini that is complimentary to an internal sequence within the aptamer. In one implementation, in the absence of target the modified aptamer preferentially adopts a stem-loop structure stabilized by terminal complimentary sequences and inhibiting fluorescence from a dye/quencher pair conjugated to the two termini. In the presence of target the ligand-binding conformation of the aptamer is favored, enhancing fluorescence. It thus appears that the ability to modify aptamers such that target binding releases a blocker oligonucleotide is a general phenomenon and thus that the detector architecture provides a straightforward means of converting any well-folded aptamer into a sensitive, selective, reagentless, electronic detector.

In one implementation of the invention, a signal-on detector is constructed by covalently attaching a single stranded thiolated sensor oligocleotide to an electrode. Then a redox-labeled, complementary blocker oligonucleotide is added to the system, hybridizing to the immobilized probe and forming a stiff double stranded complex with the electrode-bound sensor. This redox-labeled blocker hybridizes with both an electrode-proximal region and an electrode-distal region of the immobilized sensor in order to link the electrochemical redox moiety to the electrode. After hybridization, the formation of these regions of rigid, duplex DNA prevents the redox moiety from approaching the electrode surface (FIG. 1), producing only minimal Faradaic currents (a signal-off state). When a target is added, the target, which, preferably but not necessarily, is fully complementary to the immobilized sensor oligonucleotide. The hybridization of target is sufficient to break the electrode-distal region of hybridization between the redox-labeled blocker oligonucleotide and the immobilized sensor, thus liberating the redox-labeled of the blocker oligonucleotide, producing a flexible, single-stranded element. This, in turn, allows the redox moiety to collide with the electrode surface, producing a readily detectable Faradaic current (a signal-on state).

An exemplary implementation of this signal-on detector, which comprises a 15-base target nonresponsive region of complementarity and a 7-base target-disruptable region of complementarity between sensor and blocker, produces a ~750% signal gain upon hybridization with 200 nM of its complementary target. This signal change is 20-times greater than the 35% signal change observed with the original E-DNA detector at the same target concentration (Fan, C., Plaxco, K. W. and Heeger, A. J. (2003) "Electrochemical interrogation of conformational changes as a reagentless method for the sequence-specific detection of DNA." *Proc. Natl. Acad. Sci. USA*, 100, 9134-9137). This 20-fold increase in signal gain leads to significantly improved sensitivity. The novel detector architecture of the present invention permits detection of target at concentrations as low as 400 fM. The dynamic range of the dual-complementarity detector covers target DNA concentrations ranging from 800 fM to 400 nM. In contrast, control experiments reveal that the addition of a significantly mismatched target DNA at a concentration of 100 nM does not produce any significant signal change. It is anticipated that slightly mismatched targets (one or two bases out of 10) can produce a signal, albeit a much smaller signal than observed for the fully complimentary target.

Because signal generation in the detectors of the invention relies on sequence-specific interactions, the detector is quite insensitive to non-specific binding and readily detects target DNA at very low concentrations. In contrast to prior reagentless, signal-on electrochemical DNA detection schemes based on hairpin formation in a DNA-PEG-DNA block copolymer, this approach generates an dramatic change of electrochemical signal via a simple target-induced strand displacement, leading to significantly improved sensitivity. The present invention also provides a general means to evaluate any target based on a target-induced conformational change that can be monitored electronically. Moreover, the underlying detection design described herein may provide a new alternative to the conventional sandwich assay that is currently used in electronic DNA detection.

These are but four representative configurations for the signal-on E-DNA detector. Any scheme which will present different configurations in the presence and absence of target, and that repositions or allows the respositioning of a redox moiety in such a way as to increase the transfer of electrons to the sensing electrode can be used. An aspect of the detectors of this invention is the electrochemical detection of a target-induced strand displacement. This means that this invention may be generalizable to other types of redox moietys and other types of analytes, including those that are better recognized using aptamers or ribozymes or DNAzymes, where strand displacement can be induced.

The oligonucleotides of the invention may be branched or linear, natural or synthetic. The detectors may utilize any oligonucleotide capable of forming specific interactions via the nucleobases of one strand with the nucleobases of a second strand. Typically, complementary nucleic acid strands anneal to one another adhering, in general, to the Watson-Crick rules of base pairing. Stability of the double-stranded complexes is correlated with the temperature at which the strand dissociate, i.e. melting temperature ($T_m$) and is defined as the temperature at which half of the (potentially) double-stranded complexes are dissociated. As a general rule, the $T_m$ is equivalent to the sum of 2° C. for each A-T (or A-U) base pair and 4° C. for each G-C base pair. Actual $T_m$ can vary depending on ionic concentration, pH, length of the complementary sequences, G-C content and mismatches between the strands.

The oligonucleotides of the invention may also comprise an aptamers. DNA or RNA aptamers are readily available. In vitro selection techniques are able to isolate highly affinitive RNA or DNA aptamers that bind almost any arbitrary small molecule, biomacromolecule or cell type. Many aptamers undergo significant conformational changes upon analyte binding. Alternatively, although insignificant signal changes are expected for aptamers that undergo subtle conformational changes, it is feasible to accomplish analyte detection via combining an aptamer self-assembly approach [Stojanovic, M. N., de Prada, P. & Landry, D. W., *J. Am Chem. Soc.* 122, 11547-11548 (2000)]. For example, aptamers rationally dissected into two halves, with one immobilized at electrode surfaces and the other tagged with electroactive label, are expected to be split in the absence of analytes while self-assembled upon analyte binding. Thus the approach described here can be generalized to DNA and RNA aptamers and thereby to sensing platforms directed against essentially any water soluble analyte.

In some embodiments, the probe structure comprises an oligonucleotide of neutral peptide nucleic acid (PNA) or other neutral nucleic acid analog in place of the DNA blocker to allow hybridization to occur at ambient ionic strengths. PNA is chemically and enzymatically robust and, because it is uncharged, forms stronger duplexes with DNA or RNA than ssDNA.

The oligonucleotide may be attached to the electrode via a "molecular-wire" such as, for example, an oligo(phenylene vinylene) in order to facilitate electron transfer.

In the embodiments described in the examples, the redoxable chemical moiety was methylene blue. More generally, any redoxable chemical moiety that is stable under assay conditions can be used. Examples include, but are not limited to, purely organic redox moieties, such as viologen, anthraquinone, ethidium bromide, daunomycin, methylene blue, and their derivatives, organo-metallic redox moieties, such as ferrocene, ruthenium, bis-pyridine, tris-pyridine, bis-imidizole, and their derivatives, and biological redox moieties, such as cytochrome c, plastocyanin, and cytochrome c'.

The redox moiety can be attached to the blocker or sensor oligonucleotide at the 3' or 5' end of the molecule or at any internal location. For example, an oligonucleotide can include one or more modified nucleotide having a ferrocene substitution on the sugar ring. The sensor, the blocker or both can be attached to the electrode. Alternatively the sensor and blocker can be covalently attached to one another and also attached to the electrode via a single attachment point. The attachment to the electrode can be covalent or non-covalent, but preferably is through an interaction stronger than that between the sensor and blocker or sensor and target. As used herein, the term covalent attachment includes the Au—S interaction between a gold electrode and a thiolated oligonucleotide.

The electrode can be fabricated from known conductive and semiconductive materials such as, for example, gold, silver, platinum, carbon, or silicon. The conductive and semiconductive materials can be metallic or non-metallic. Gold gives good results. The surface of the electrode preferably is functionalized with the oligonucleotide probe structure through self-assembly, such as through the well-established gold-S chemistry of self assembly.

It is also commonly preferred that the electrode surface, functionalized with the oligonucleotide probe structure, is subsequently passivated by materials such as 2-mercaptoethanol, (2-ME), 6-mercaphohexanol or mercaptoalkanols generally (HS—$(CH_2)_n$—OH with n=2~18) and the like. In certain implementations, the electrode is capable of inducing redox events in the redox moiety.

In one implementation of the detector, a gold electrode is employed. To fabricate the detector, a clean gold surface can reacted with a solution of thiolated oligonueclotide sensor. The oligonucleotide preferably is thiolated at the 3' or 5' end. However, in certain configurations, the thiol need not be at the extreme end of the oligonucleotide. A weak reducing agent, tris-(2-carboxyethyl) phosphine hydrochloride (TCEP) can be included with the solution of thiolated oligonucleotide to discourage disulfide bonding between oligonucleotides from forming. Exemplary reaction conditions for attaching thiolated oligonucleotides to the gold electrode include 200 mM Tris-HCl buffer, pH 7.4, for 16 hours at room temperature. The resulting surface can be washed, e.g., with the Tris-HCl buffer. The functionalized gold surface can be treated with 1 mM 1-mercaptohexanol in 10 mM Tris-HCl buffer, pH 7.4, for 1 hour to passivate the electrode surface and to increase the stability of the gold-thiolated DNA bond by improved packing. Once a monolayer-functionalized surface is prepared, the second oligonucleotide is hybridized to the attached oligonucleotide. Exemplary hybridization conditions include 1.0 μM, in Perfect Hyb™ plus hybridization buffer (Sigma-Aldrich Inc, Milwaukee, Wis.) (1×), for 3 hours to yield the double-stranded blocker-sensor assembly on the electrode surface.

Because strand displacement involves an electronic sensor (e.g., a redoxable moiety), advances in electrophoretically-improved hybridization times can be applied (Cheng, et al., *Nuc. Acid Res.*, 22:380-385 (1996); Cheng, et al., *Nat. Biotech.* 16:541-546 (1998)). Moreover, because of its direct integration into electronics and excellent scalability and the turn on detectors' impressive signal strength suggests that significantly smaller electrodes can be employed) and is well suited for applications in electronic gene detection arrays. To this end, biomaterials can be deposited onto specific pixels of gold "nanode" arrays and electrochemically addressed.

In a more preferred embodiment, the microelectrodes are arrayed in the format of N "pixels" with each pixel containing a unique oligonucleotide structure and with all microelectrodes electrochemically addressable, thereby enabling detection of N different targets.

D. Methods of Detecting a Target

One aspect of the invention provides methods for assessing the presence of a molecular target in a sample comprising the steps of (a) contacting the sample with a detector of the invention and (b) sensing a first redox signal with the detector, wherein the first redox signal is indicative of the presence of the molecular target in the sample. In certain implementations, the methods can further comprise the steps of (c) contacting a standard with the detector; (d) sensing a second redox signal with the detector; and (e) comparing the first redox signal to the second redox signal. In a preferred implementation, the standard contains a known amount of the molecular target and comparing the first redox signal to the second redox signal comprises correlating a similarity in the first and second redox signals with a similar level of the molecular target in the sample and the standard. Preferably, the standard contains no molecular target and comparing the first redox signal to the second redox signal comprises correlating a similarity in the first and second redox signals with an absence of molecular target in the sample and a difference in the first and second redox signals with the presence of the molecular target in the sample.

The strand displacement events that are sensed by the detectors, and methods of this invention, are carried out in liquid environments. Aqueous environments are preferable but optionally rendered at least somewhat ionic by the presence of dissolved salt. It is generally understood that ionic environments favor hybridization. "Salt" is defined to include sodium chloride but also any other water-soluble alkaline earth or alkyl metal ionic materials or charged organic materials. Magnesium, potassium, calcium, and/or manganese salts may be particularly useful for practicing the invention. While there may be advantages to particular salt materials or levels, they are not seen to be critical to the practice of this invention. Representative salt levels can be as high as about 4 or 5 molar, in some cases and as low as nearly zero. Salt levels of from about 0.05 to about 2 molar are presently preferred. In a particular embodiment of the invention, a physiological salt concentration (i.e., about 150 mM) is used. In other embodiments of the invention, the salt concentrations may bracket physiological salt conditions, e.g., from about 75 mM to about 300 mM.

Target binding and strand displacement can be carried out in the presence of agents and additives that promote the desired hybridization or binding, diminish nonspecific background interactions, inhibit the growth of microorganisms, or increase the stability of the probe and/or target oligonucleotides. For example, one can add up to 10% by weight or volume (based on the amount of aqueous environment) and particularly from about 1 or 2% to about 10% of one or more polyols. Representative polyols include glycerol, ethylene glycol propylene glycol sugars such as sucrose or glucose, and the like. One can also add similar levels of water soluble or water dispersible polymers such as polyethylene glycol (PEG) or polyvinyl alcohol or the like. Another representative additive is up to about 1 or 2% by weight (again based on the liquid substrate) of one or more surfactants such as triton X-100 or sodium dodecyl sulfate (SDS). All of these agents are electrochemically silent at the potentials observed with the detectors and methods of the invention. A variety of hybridization conditions have been described and are well known in the art. Many such hybridization conditions are useful for practicing the invention.

Target binding and the associated strand displacement can be carried out at ambient temperature, although any temperature in the range over which the sensor and the sensor strand-target complex are stable can be used. A preferred range is from about 5 to about 45° C. Increased temperatures can improve the specificity of recognition for DNA and some other targets. Reaction times should be a short as possible for convenience. Times as short as minutes (e.g., about 1 to 5 minutes) can be used. Times of up to 5, 10, 15, 20, 30, 45, or 60 minutes, or longer may also be used. We have had good results with reaction times of from about 15 to about 45 minutes. Temperatures and times may be determined empirically or using, e.g., CoT analysis or other methods of predicting hybridization conditions.

False positives can be identified via multiplexing, e.g., using multiple, electrochemically distinct labels, such that the sensor and one or more control elements are integrated into a single detector pixel. By employing multiple labels with narrow, non-overlapping redox potentials, 2-5 or possible more distinct sequences can be simultaneously interrogated on a single electrode. This enables the inclusion of internal controls, e.g., for DNA detection this would include elements that are not complementary to known sequences that would respond to false positives arising due to non-specific disruption or degradation of sensor and/or blocker strand. Multiplexing will also facilitate signal redundancy, alleviating the risk of masking in the unlikely event of contaminants with redox potentials precisely where the primary label reports. In addition to exhibiting narrow, non-overlapping redox peaks, the appropriate labels for multiplexing should be stable and synthetically facile. Electroactive labels that meet these requirements, include a large number of ferrocene (Brazill, et al., *Anal Chem.* 73, 4882-4890 (2001)) and viologen derivatives (Fan, et al., *Langmuir* 19, 3554-3556 (2003)) and any redoxable species, such as methylene blue, anthraquinone, ethidium bromide, daunomycin.

AC voltammetric methods are commonly employed in an effort to delineate between redox and charging currents based on the different timescales for the two processes. Double-layer formation is limited only by ion mobility and thus equilibrates rapidly, whereas redox currents are limited by Marcus-type barriers and is orders of magnitude slower. Sinusoidal voltammetry (SV) or pulsed voltammetry has proven particularly useful; in addition to the SV frequency spectrum, time course data is obtained at each harmonic frequency element by performing the digital equivalent of a lock-in amplifier (Brazill, et al. *J. Electroanal. Chem.*, 531:119-132 (2002)). That is, the instantaneous current is monitored at the optimum phase angle for the signal of interest, thus greatly increasing the sensitivity and selectivity over traditional voltammetric techniques. This temporal deconvolution enables a large increase in peak to charging current ratios and thus an improvement in sensor sensitivity by orders of magnitude. For many implementations optimization of the AC frequency can lead to significant improvements in sensor performance, including significant reductions in background current arising from the target-free sensor-blocker complex. Cyclic voltammetry is also used.

As demonstrated in the following examples, detectors of the invention are both sensitive and highly selective. The sensitivity and selectivity of the detector is better than that of typical CCD-based fluorescent detectors, and is comparable to a recently proposed, conjugated polymer-based fluorescence amplification method (Gaylord, et al., *Proc. Nat. Acad. Sci. U.S.A.* 99:10954 (2002); Moon, et al., *Chem. Commun.*, 2003 Jan. 7; (1): 104-5). The key sensing element, e.g., an oligonucleotide associated with a redoxable moiety, is compatible with normal solid-state synthesis of oligonucleotides. Moreover, the surface assembly process is robust and facile.

Since the entire set-up can be conveniently prepared and is generally compatible with chip-based technology, the novel, reagentless detection described here provides a promising alternative to fluorescence-based detectors for most if not all of their applications.

This invention will be further described by the following examples. These are presented to illustrate the general practice of this invention and are not to be construed as limitations upon its scope.

EXAMPLES

A. Example 1

Reusable Reagentless Detector

Modified DNA oligonucleotides were synthesized by Bio-Source, Int. (Foster City, Calif.), purified via C18 HPLC and PAGE, and confirmed by mass spectroscopy. The sequences of these three oligonucleotides employed are given below:

```
SEQ ID NO. 1: 5'-HS-(CH2)6GCGAGGTAAAACGACGGCCAGTCTC
              GC-(CH2)7-MB-3'

SEQ ID NO. 2: 5'-CCCTATGTATGCTCTTTGTTGTGGCGAGACTGG
              C-3'

SEQ ID NO. 3: 5'-GCCAGTCTCGCCACAACAAAGAGCATACATAGG
              G-3'
```

The detector was fabricated using polycrystalline gold disk electrodes (1.6 mm diameter, BAS, West Lafayette, Ind.). The electrodes were prepared by polishing with diamond and alumina (BAS), sonicating in water, and electrochemically cleaning (a series of oxidation and reduction cycling in 0.5 M NaOH; 0.5 M $H_2SO_4$; 0.01 M KCl/0.1 M $H_2SO_4$; and 0.05 M $H_2SO_4$) before being modified with the thiolated probe DNA. To fabricate the detectors a clean gold surface was reacted with a solution of thiolated blocker DNA (SEQ ID NO: 1), 0.5 µM including 5 µM TCEP (tris-(2-carboxyethyl) phosphine hydrochloride, which is included to reduce disulfide bonded oligonucleotides[1]) in 200 mM Tris-HCl buffer, pH 7.4, for 16 hrs at room temperature. The resulting surface was washed with the Tris-HCl buffer, and then the blocker oligonucleotide-functionalized gold-surface was treated with 1 mM 6-mercaptohexanol in 10 mM tris-HCl buffer, pH 7.4, for 2 hrs. Electrochemical measurements indicate that the surface coverage of blocker DNA on the electrode surface is ca. $(9.0\pm0.2)$ pmole·$cm^{-2}$. The resulting monolayer-functionalized surface was treated with the complementary sensor DNA (SEQ ID NO. 2), 2.5 µM, in Perfect Hyb™ plus hybridization buffer (Sigma) (1×), for 6 hrs to yield the final duplex DNA probe assembly on the surface. The duplex DNA surface was then allowed to hybridize with various concentrations of target DNA (SEQ ID NO. 3), in Perfect Hyb™ plus hybridization buffer (Sigma) (1×), for 16 hrs to obtain the maximum strand-displacement on the surface.

Detector measurements were conducted by monitoring the electrode in 0.1 M NaCl+10 mM PB (pH 7.4). Electrodes were incubated in each target DNA sample (200 µl total volume) for 16 hrs at room temperature before target detection measurements were performed. The results of these measurements are show in FIG. 5.

Figure 5:
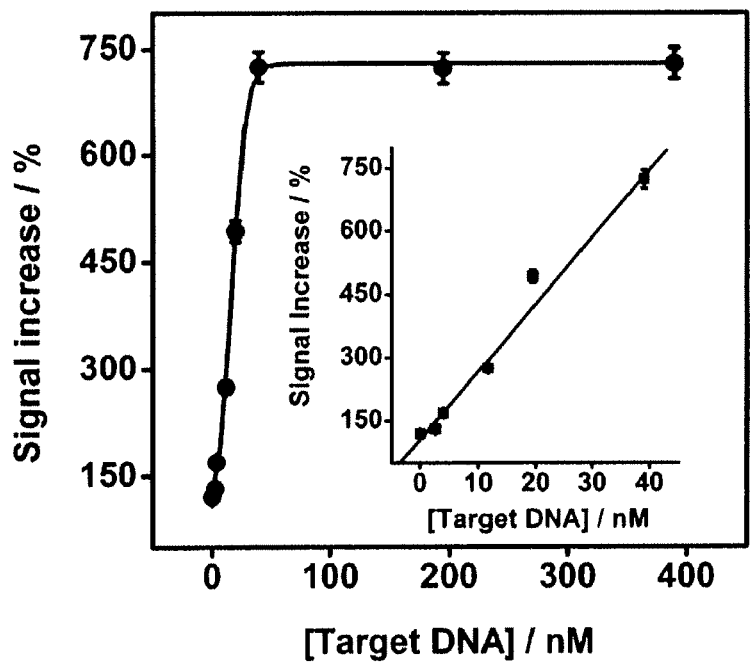
FIG. 5 graphically illustrates that the dynamic range of one implementation of the detector configured as in scheme B covers target concentrations which range from 4 nM to 400 nM. The error bars represent the standard deviation of 4 measurements conducted with a single electrode at each target DNA concentration.

As shown in FIG. 5, the dynamic range of the hairpin-based detector covers target concentrations which range from 4 nM to 400 nM. The error bars represent the standard deviation of four measurements conducted with a single electrode at each target DNA concentration. Multiple electrodes were used to collect this data set.

B. Example 2

Dual Complementarity Region Detector

Modified DNA oligonucleotides were synthesized by BioSource, Int. (Foster City, Calif.), purified via C18 HPLC and PAGE, and confirmed by mass spectroscopy. The sequences of these three oligonucleotides employed are given below:

SEQ ID NO. 4: 5'-HS-(CH$_2$)$_6$-GCGAGTTAGACCGATCCCCCCCT TCGTCCAGTCTTTT-3'

SEQ ID NO. 5: 5'-MB-(CH$_2$)$_6$-GACTGGACGCCCCCCCATCGGTCT AACTCGC-3'

SEQ ID NO. 6: 5'-AAAAGACTGGACGAA-3'

The detector was fabricated using polycrystalline gold disk electrodes (1.6 mm diameter, BAS, West Lafayette, Ind.). The electrodes were prepared by polishing with diamond and alumina (BAS), sonicating in water, and electrochemically cleaning (a series of oxidation and reduction cycling in 0.5 M NaOH; 0.5 M H$_2$SO$_4$; 0.01 M KCl/0.1 M H$_2$SO$_4$; and 0.05 M H$_2$SO$_4$) before being modified with the thiolated sensor DNA. To fabricate the detectors a clean gold surface was reacted with a solution of thiolated sensor DNA (SEQ ID NO. 4), 0.5 µM including 5 µM TCEP (tris-(2-carboxyethyl) phosphine hydrochloride, which is included to reduce disulfide bonded oligonucleotides) in 200 mM Tris-HCl buffer, pH 7.4, for 16 hrs at room temperature. The resulting surface was washed with the Tris-HCl buffer, and then the sensor-functionalized gold-surface was treated with 1 mM 6-mercaptohexanol in 10 mM tris-HCl buffer, pH 7.4, for 2 hrs. The resulting monolayer-functionalized surface was treated with the complementary blocker DNA (SEQ ID NO. 5), 2.5 µM, in Perfect Hyb™ plus hybridization buffer (Sigma) (1×), for 6 hrs to yield the final duplex DNA probe assembly on the surface. The duplex DNA surface was then allowed to hybridize with various concentrations of target (SEQ ID NO. 6), in Perfect Hyb™ plus hybridization buffer (Sigma) (1×), for 16 hrs to obtain the maximum strand-displacement on the surface.

Detector measurements were conducted by monitoring the electrode in 0.1 M NaCl+10 mM PB (pH 7.4). Electrodes were incubated in each target DNA sample (200 µl total volume) for 16 hrs at room temperature before target detection measurements were performed. The results of these measurements are show in FIG. 6.

Figure 6:
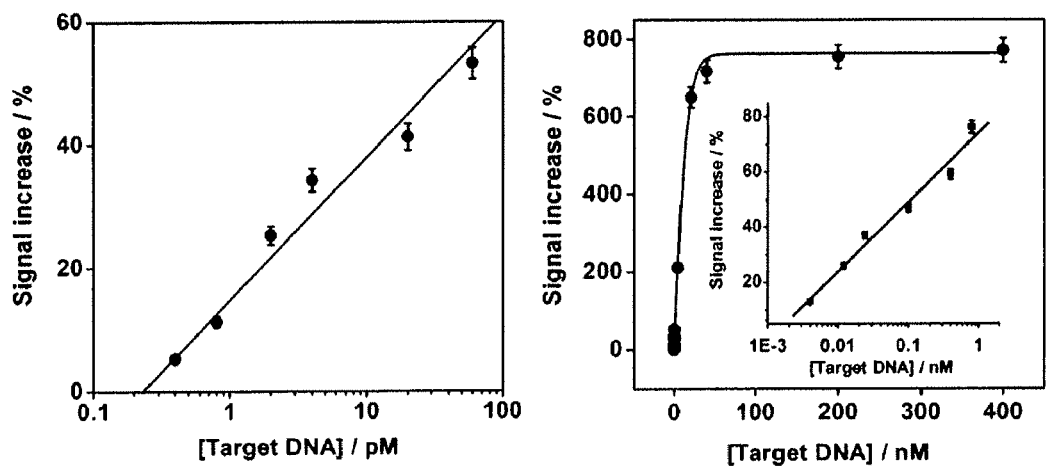
FIG. 6 graphically illustrates that the dynamic range of one implementation of a detector configured as in scheme A covers target concentrations which range from 800 fM to 400 nM. The error bars represent the standard deviation of 4 measurements conducted with a single electrode at each target DNA concentration.

FIG. 6 shows that the dynamic range of the detector covers target concentrations which range from 800 fM to 400 nM. The error bars represent the standard deviation of four measurements conducted with a single electrode at each target DNA concentration. Multiple electrodes were used to collect this data set.

C. Example 3

Aptamer-Based Detector

Labeled DNA oligonucleotides were synthesized by BioSource, Int. (Foster City, Calif.), and purified via C18 HPLC and PAGE, and confirmed by mass spectroscopy. The sequences of these three oligonucleotides employed are given below:

SEQ ID NO. 7: 5'-HS-(CH$_2$)$_6$-CCATCTCCACTTGGTTGGTGTGG TTGG-3'

SEQ ID NO. 8: 5'-MB-(CH$_2$)$_2$-CCAACTTTTAAGTGGAGATGG-3'

SEQ ID NO. 9: 5'-HS-(CH$_2$)$_6$-CCATCTCCACTTGGTGGTGGTTG TGGT-3'

SEQ ID NO. 10: 5'-MB-(CH$_2$)$_2$-ACCACTTTTAAGTGGAGATGG-3'

The detector was fabricated using polycrystalline gold disk electrodes (1.6 mm diameter, BAS, West Lafayette, Ind.). The electrodes were prepared by polishing with diamond and alumina (BAS), sonicating in water, and electrochemically cleaning (a series of oxidation and reduction cycling in 0.5 M NaOH; 0.5 M H$_2$SO$_4$; 0.01 M KCl/0.1 M H$_2$SO$_4$; and 0.05 M H$_2$SO$_4$) before being modified with the thiolated DNA. The clean gold surface was interacted with a solution of thiolated thrombin aptamer sensor (SEQ ID NO. 7), 0.8 µM including 8 µM TCEP (tris-(2-carboxyethyl) phosphine hydrochloride, which is included to reduce disulfide bonded oligos) in 200 mM Tris buffer, pH 7.4, for 16 hrs. The surface was then rinsed with deionized water and subsequently passivated with 6-mercaptohexanol (1 mM in 10 mM Tris buffer, pH 7.4) for 1 hrs. The electrodes were then rinsed again with 10 mM Tris buffer, pH 7.4. The resulting monolayer-functionalized surface was treated with the MB-tagged blocker DNA (SEQ ID NO. 8), 1.0 µM, in Perfect Hyb™ plus hybridization buffer (Sigma) (1×), for 3 hours to yield the ds-DNA-aptamer assembly on the surface. Control electrodes modified with oligonucleotide (SEQ ID NO. 9) and (SEQ ID NO. 10) were prepared in an identical fashion.

Detector measurements were conducted using alternating current voltammetry (ACV) with a CHI 603 potentiostat (CH Instruments, Austin, Tex.) in a standard cell with a platinum counter electrode and a Ag/AgCl reference electrode. All measurements were conducted by monitoring the electrode in 20 mM Tris, pH 7.4 with 140 mM NaCl, 20 mM MgCl and 20 mM KCl. For all thrombin detection measurements, electrodes were incubated in each sample in 20 mM Tris, pH 7.4 with 140 mM NaCl, 20 mM MgCl and 20 mM KCl for 3 hrs at 37° C.

Figure 7:
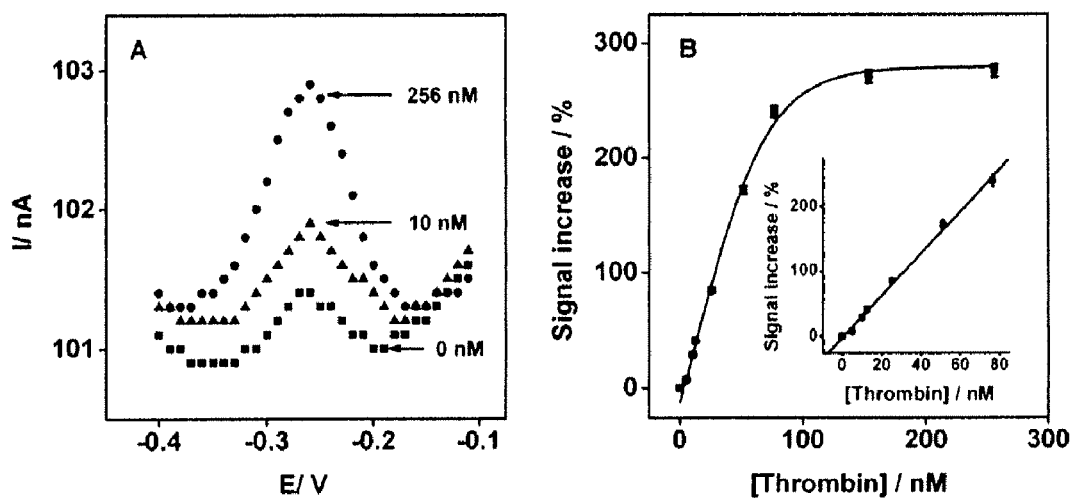
FIG. 7A provides alternating current voltammetric (ACV) curves of the ds-DNA-aptamer functionalized surfaces in the embodiment of FIG. 4 obtained in 20 mM Tris-HCl, pH 7.4 with 140 mM NaCl, 20 mM MgCl and 20 mM KCl at various thrombin concentrations.
FIG. 7B illustrates a dose-response curve for the same signal-on thrombin detector. The illustrated error bars represent the standard deviation of 4 measurements conducted with a single electrode at each thrombin concentration.

The signal-on detector, having oligonucleotides of SEQ ID NO. 7 and SEQ ID NO. 8, is responsive to its molecular target. In the absence of thrombin, only small, highly reproducible (standard deviation across 4 electrodes ~4%) Faradaic currents are observed (FIG. 7A, 0 nM thrombin). This residual peak may arise because the surface-immobilized aptamer (SEQ ID NO. 7) is in a conformational equilibrium between a duplex DNA and the binding-competent G-quadruplex. As thrombin is added to the solution, the surface loading of bound thrombin increases, boosting the Faradaic current until a 3-fold signal gain is obtained at a target concentration of ~260 nM. FIG. 7A shows alternating current voltammetric (ACV) curves of the ds-DNA-aptamer functionalized surfaces obtained in 20 mM Tris-HCl, pH 7.4 with 140 mM NaCl, 20 mM MgCl and 20 mM KCl at various thrombin concentrations. FIG. 7B illustrate a dose-response curve for the signal-on E-AB thrombin detector. The illustrated error bars represent the standard deviation of four measurements conducted with a single electrode at each thrombin concentration. Multiple electrodes were used to collect the entire data set. (Relative detector response, in percent change, is employed because this is more reproducible electrode-to-electrode than absolute current change, which depends sensitively on total electrode area.)

In contrast to a previously described, signal-off detector, for which thrombin concentrations of as high as 800 nM produce only a 40% signal decrease, the signal-on detector of the invention produces an approximately 270% signal gain at only 256 nM thrombin. This improved signal gain leads to improved signal robustness and sensitivity. For example, whereas 19 nM thrombin produces only a 7% signal drop in the signal-off detector, this same target concentration produces a 60% signal increase in the new architecture. As a result, the signal-on detector permits detection of thrombin at concentrations as low as 3 nM. The dynamic range of the aptamers-based detector (FIG. 7B) covers physiologically relevant concentrations, which range from a few nanomolar in resting blood to several hundred nanomolar when the clotting cascade is activated.

Figure 8:
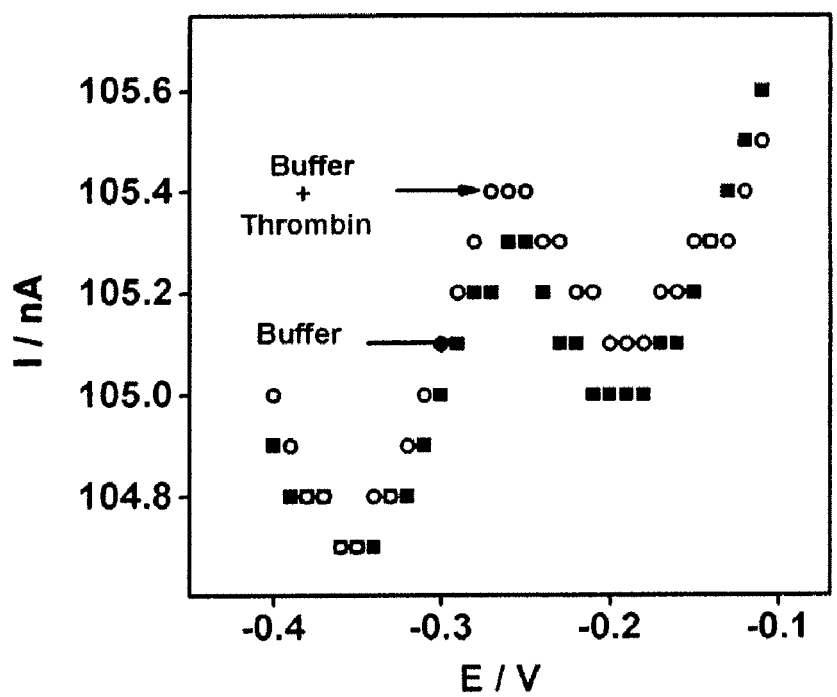
FIG. 8 graphically illustrates that the control detector, made by thiolated control (non-thrombin-binding) oligonucleotide and its complementary MB-tagged DNA, does not exhibit any significant signal change even when challenged with 76 nM of the target protein. Shown is the detector electrochemical signal arising from thrombin-free buffered saline and from the same buffer doped with 76 nM thrombin.

Control experimental results obtained using this detector are shown in FIG. 8. Control experiments shown in FIG. 8 reveal that, when coupled with its complementary MB-tagged DNA (SEQ ID NO. 10), a thiolated oligonucleotide (SEQ ID NO. 9) of identical sequence composition and 81% sequence identity with the thrombin aptamer (SEQ ID NO. 7) but known not to bind to thrombin, does not exhibit any measurable signal change when challenged with thrombin.

Figure 9:
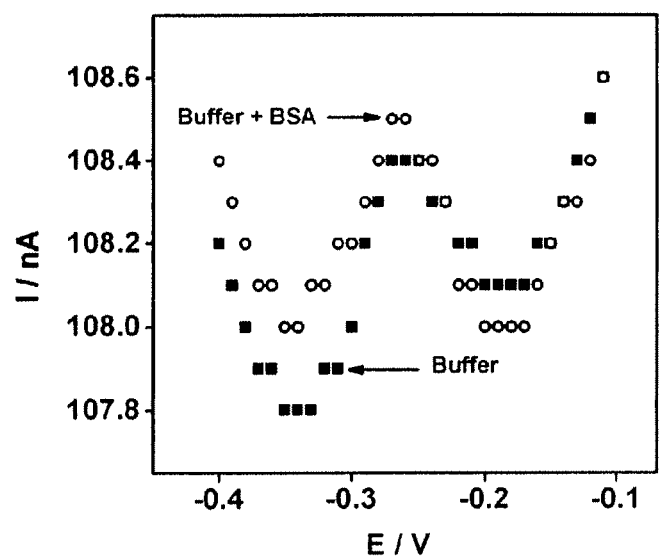
FIG. 9 graphically illustrates that the control detector made by thiolated control oligonucleotide and its complementary MB-tagged DNA does not exhibit any measurable signal change when challenged with BSA. Shown is the detector electrochemical signal arising from thrombin-free buffered saline and from the same buffer doped with 0.3 uM BSA.

Further control experimental results obtained using this detector are shown in FIG. 9 FIG. 9 graphically illustrates the results of experiments demonstrating that a sensor comprised of the proper thiolated oligonucleotide (SEQ ID NO. 7) and its complementary MB-modified DNA (SEQ ID NO. 8) does not exhibit any measurable signal change when challenged with BSA. Shown is the detector electrochemical signal arising from thrombin-free buffered saline and from the same buffer doped with 0.3 μM BSA. This implies that release of the MB redox moiety and the subsequent increase in electron transfer require the formation of a specific aptamer-thrombin complex.

D. Example 4

Lead Ion-Responsive, DNAzyme-Based Detector

Labeled DNA oligonucleotides were synthesized by BioSource, Int. (Foster City, Calif.), and purified via C18 HPLC and PAGE, and confirmed by mass spectroscopy. The sequences of the modified DNA catalytic (sensing) strands are given below:

SEQ ID NO. 11:   5'-HS-(CH$_2$)$_6$-TTTCATCTCTTCTCCG-AGCC
                  GGTCGAAATAGTGAGT-(CH$_2$)$_2$-MB-3'

SEQ. ID NO. 12:  5'-HS-(CH$_2$)$_6$-TTTCATCTCTTCCCCGAG-CC
                  GGTCGAAATAGTGAGT-(CH$_2$)$_2$-MB-3'

MB was conjugated to the 3' end of these probes via succinimide ester coupling (MB-NHS obtained from EMP Biotech, Germany).

The chimeric DNA and unmodified DNA blocker (substrate) strands were purchased from Integrated DNA Technologies Inc., and were purified by RNase Free HPLC by the company. The sequences of these DNA are given:

SEQ ID NO. 13:   5'-ACTCACTATrAGGAAGAGATG-3'
SEQ ID NO. 14:   5'-ACTCACTATAGGAAGAGATG-3'

The $Pb^{2+}$-requiring "8-17" DNAzyme is a sequence-specific nuclease acting on a single-stranded DNA substrate containing a single, scissile ribo-adenine. The sensor consists of a methylene-blue (MB) modified version of this catalytic sensor strand (SEQ ID NO. 11) hybridized to its complementary, 20-base substrate (blocker) oligonucleotide (SEQ ID NO; 13). This complex, which is chemi-absorbed to a gold electrode via a 5' terminal thiol on the catalytic strand, is relatively rigid, preventing the MB from approaching the electrode to transfer electrons (FIG. 3). In the presence of $Pb^{2+}$, the trans-acting catalytic strand cleaves the scissile phosphodiester of the substrate blocker strand into two fragments (FIG. 3B). These fragments dissociate from the complex, allowing the MB on the sensor strand to transfer electrons to the electrode.

The catalytic sensor strand (SEQ ID NO. 11) was designed as a functional domain of 15 deoxynucleotides flanked by substrate-recognition domains of 9 nucleotides each at the 3' and 5' termini. Previous studies indicate that this represents the optimal compromise between stable complex formation and efficient dissociation after cleavage (Breaker, et al. *Chem. Biol.* 1:223-229 (1994); Santoro et al. *Proc. Nat'l Acad. Sci. USA* 94:4262-4266 (1997). As determined by electrochemical measurements, the surface coverage of the MB-modified catalytic sensor strand (SEQ ID NO. 11) was maintained within the range of 3.8±0.3 pmol·cm$^{-2}$, an electrode loading level at which sensor gain is maximized.

Figure 10:
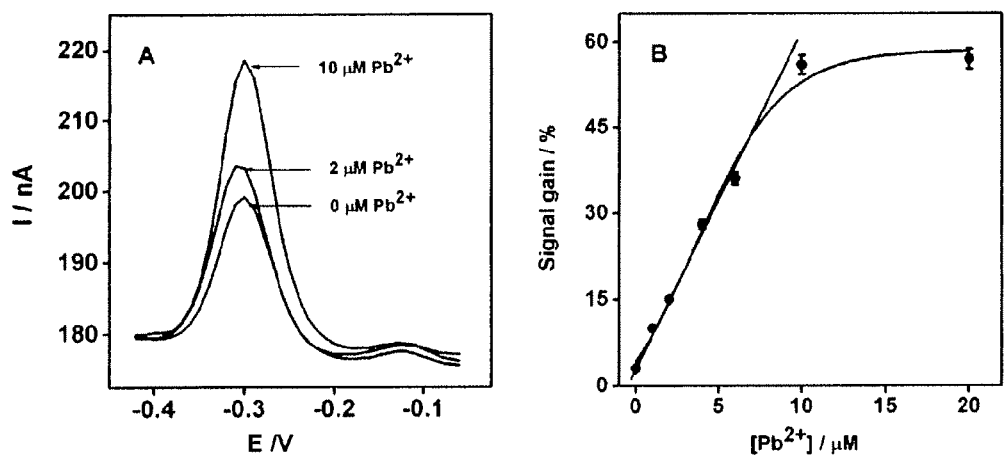
FIG. 10 graphically illustrates that the target-induced response of one implementation of the detector configured as in scheme C directed against the target lead ($Pb^{2+}$).
Figure 11:
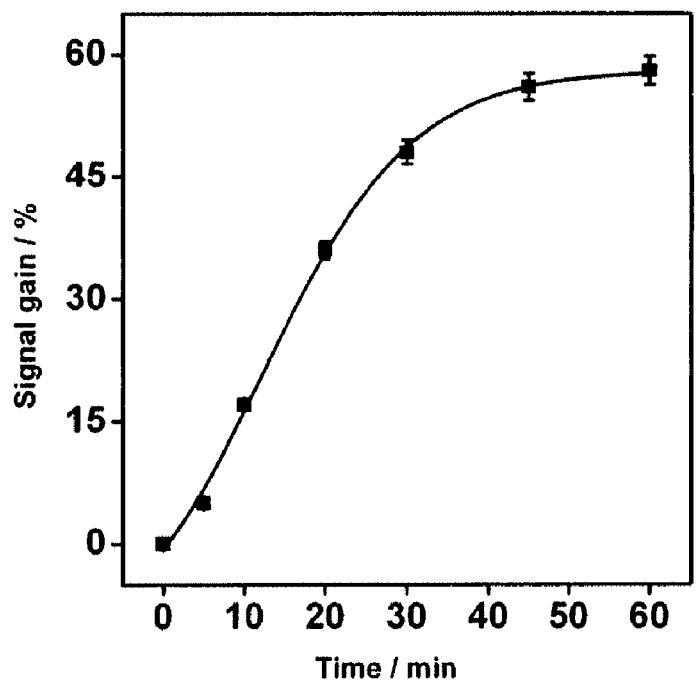
FIG. 11 demonstrates that one implementation of the detector configured as in scheme C responds rapidly to its target.

The DNAzyme-based signal-on detector is sensitively and specifically responsive to its target ion (FIG. 10). In the absence of $Pb^{2+}$, only small, reproducible Faradaic currents can be observed. Upon increasing $Pb^{2+}$, a large increase Faradaic current is generated, saturating at a ~60% signal increase above 10 μM. The directly measured detection limit of the current detector architecture after 1 hr incubation at 37° C. is 0.3 μM (62 ppb) and the signal gain is linear over the range from 0.5 to 10 μM (104 to 2070 ppb). While these values were obtained after 1 hr incubations, the detector is reasonably rapid, with the majority of the signal change occurring within minutes (FIG. 11).

Figure 12:
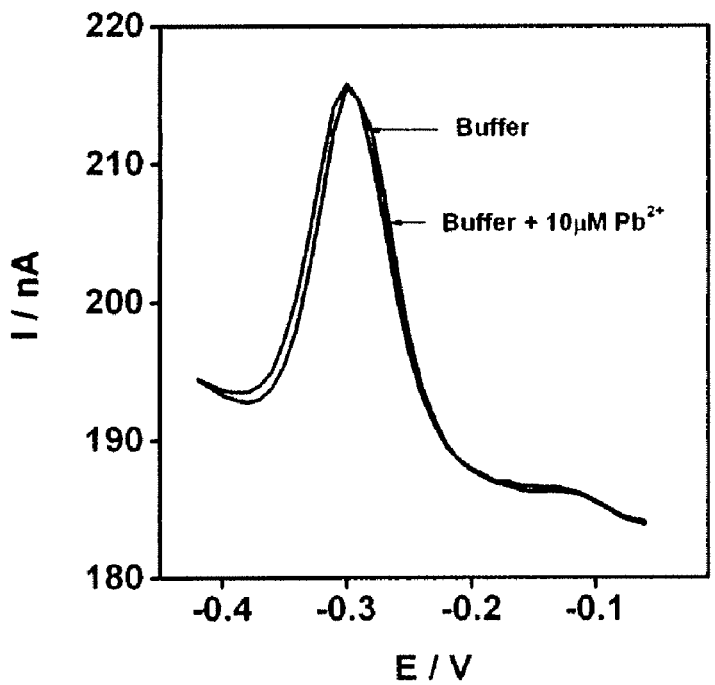
FIG. 12 demonstrates that one implementation of the detector configured as in scheme C but employing an inactivated mutant sensor strand (inactivated due to a thymine to cytosine mutation at position 13 of the DNAzyme sequence) does not respond even when challenged with 10 μM $Pb^{2+}$ FIG. 13 demonstrates that one implementation of the detector configured as in scheme C but employing an unreactive, all-deoxyribose blocker (substrate) strand fails to respond when similarly challenged with the target at 10 μM.
Figure 13:
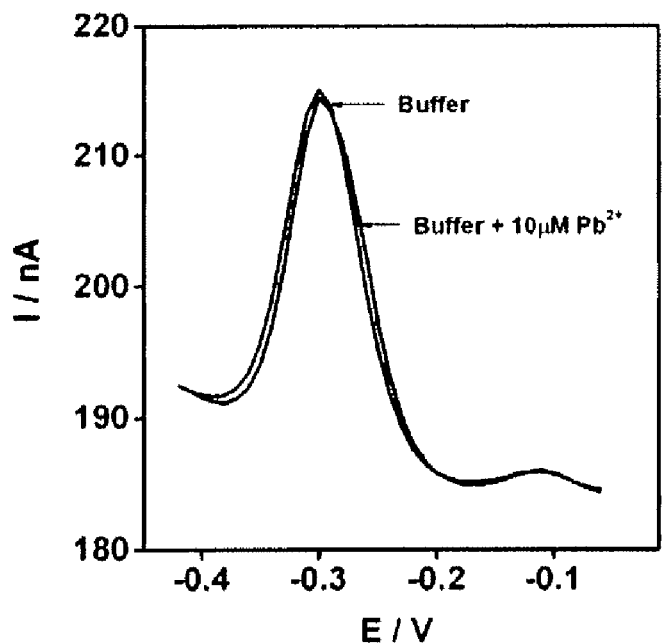

For example, detectors fabricated using an inactive mutant sensor strand (SEQ ID NO. 12) (due to a T to C mutation at position 13), does not respond even when challenged with 10 μM $Pb^{2+}$ (FIG. 12). A detector built using an unreactive, all-deoxyribose blocker strand (SEQ ID NO. 14) also fails to respond when similarly challenged (FIG. 134).

Figure 14:
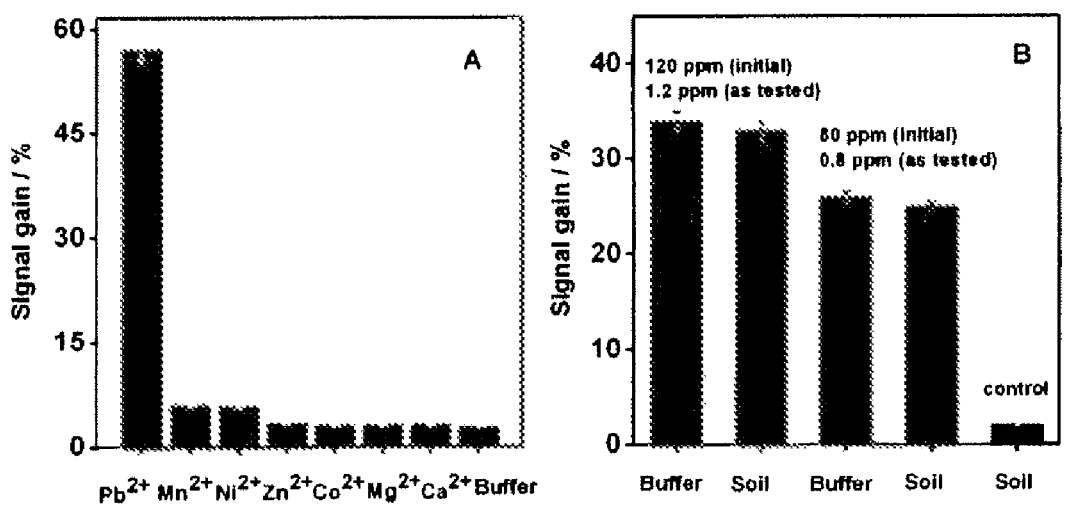
FIG. 14 demonstrates one implementation of the detector configured as in scheme C is both specific (capable of rejecting similar ions) and selective (uninhibited by complex, contaminant-ridden samples).

The specificity of the detector was determined by challenging it with the divalent metal ions $Mn^{2+}$, $Ca^{2+}$, $Mg^{2+}$, $Zn^{2+}$, $Co^{2+}$ and $Ni^{2+}$ at 10 μM concentrations. (FIG. 14A). The detector response to these ions is effectively indistinguishable from the response observed for control samples lacking exogenously added metal ions.

At 62 ppb (0.3 μM) the detection limit of the detector is more than sufficient for the routine monitoring of lead levels in food and environmental samples. For example, the US Food and Drug Administration has set an action level of 500 ppb (2.5 μM) for lead in products intended for use by infants and children. Similarly, the US Environmental Protection Agency's (EPA) action levels for total lead in soils range from 100 to 400 parts-per-million (ppm) (0.5 to 1.5 millimolar). EPA method 3050B (Method 2050B, revision 2, USEPA SW-846, December 1996, 3$^{rd}$ Edition) was used to extract the lead from standard soil sample prior to measurement. The lead in these spiked soil samples (at 80 ppm or 120 ppm) was extracted in 1 ml of 10% HOAc (to solublize the often insoluble lead salts present in soil) before being diluted 100-fold prior to analysis. Assaying the resulting samples with the detector provides values within a few percent of those determined using standard ICP/MS analysis methods (FIG. 14B).

What is claimed is:

1. A detector for assessing the presence of a molecular target comprising:
   a) an oligonucleotide blocker;
   b) an oligonucleotide sensor having:
      a first region complementary to a first region of the blocker, which first regions are capable of forming a first double-stranded complex with the blocker, wherein the first region of the sensor is capable of specifically interacting with the molecular target thereby disrupting the first double-stranded complex; and
      a second region complementary to a second region of the blocker,
      wherein the second regions forms a second double-stranded complex that is not disrupted in the presence of the molecular target; and
   c) an electrode capable of detecting redox signals from a redox moiety covalently attached to either the blocker or the sensor, wherein at least one of the sensor and the blocker is covalently attached to the electrode,
      wherein when the first double-stranded complex is formed, the redox moiety is in a first state relative to the electrode, and when the first double-stranded complex is disrupted by the molecular target, the redox moiety is in a second state relative to the electrode, wherein the first and second states give rise to distinguishable redox signals detectable by the electrode.

2. The detector of claim 1, wherein the redox moiety is covalently attached to the blocker.

3. The detector of claim 2, wherein the sensor is covalently attached to the electrode.

4. The detector of claim 3, wherein the blocker is covalently attached to the sensor.

5. The detector of claim 3, wherein the blocker is covalently attached to the electrode.

6. The detector of claim 1, wherein the oligonucleotide blocker is a linear oligonucleotide or a branched oligonucleotide.

7. The detector of claim 1, wherein the oligonucleotide sensor is a linear oligonucleotide or a branched oligonucleotide.

8. The detector of claim 1, wherein the oligonucleotide sensor is an aptamer, a DNAzyme or a ribozyme.

9. The detector of claim 1, wherein more than one redox moiety is attached to either the blocker or the sensor.

10. The detector of claim 1, wherein the redox signal detectable in the second state is greater than the redox signal detectable in the first state.

11. The detector of claim 10, wherein the redox moiety is capable of being closer to the electrode in the second state as compared to the first state.

12. The detector of claim 10, wherein the second state includes a higher level of redox moiety dynamics that enhance electron transfer from the redox moiety to the electrode as compared to the level of redox moiety dynamics in the first state.

13. The detector of claim 1, wherein the electrode is capable of inducing redox events in the redox moiety.

14. The detector of claim 1, wherein the electrode is selected from the group consisting of metallic conductors, nonmetallic conductors, metallic semiconductors and nonmetallic semiconductors.

15. The detector of claim 1, wherein the electrode comprises a metal.

16. The detector of claim 15, wherein the metal is gold.

17. The detector of claim 1, wherein the redox moiety is selected from the group consisting of purely organic redox moieties, organo-metallic redox moieties, and biological redox moieties.

18. The detector of claim 17, wherein the purely organic redox moiety is viologen, anthraquinone, ethidium bromide, daunomycin, or methylene blue.

19. The detector of claim 17, wherein the organo-metallic redox moiety is ferrocene, ruthenium, bis-pyridine, tris-pyridine, or bis-imidizole.

20. The detector of claim 17, wherein the biological redox moiety is cytochrome c, plastocyanin, or cytochrome c'.

21. A method for assessing the presence of a molecular target in a sample comprising the steps of:
   a) contacting the sample with a detector comprising
      i) an oligonucleotide reporter having a redox moiety attached;
      ii) an oligonucleotide sensor having:
         a first region complementary to a first region of the oligonucleotide reporter, which first regions are capable of forming a first double stranded complex, wherein a complementary oligonucleotide sensor is capable of specifically interacting with the molecular target thereby disrupting the first double stranded complex; and
         a second region complementary to a second region of the oligonucleotide reporter, which second regions are capable of forming a second double stranded complex that is not disrupted in the presence of the molecular target; and wherein the oligonucleotide sensor is covalently attached to an electrode; and iii) an electrode capable of detecting redox signals from the redox moiety, wherein at least one of the oligonucleotide reporter and the complementary oligonucleotide sensor is covalently attached to the electrode; and b) sensing a first redox signal with the detector, wherein the first redox signal is indicative of the presence of the molecular target in the sample.

22. The method of claim 21, further comprising the steps of c) contacting a standard with the detector; and d) sensing a second redox signal with the detector; and e) comparing the first redox signal to the second redox signal.

23. The method of claim 22, wherein the standard contains a known amount of the molecular target and comparing the first redox signal to the second redox signal comprises correlating a similarity in the first and second redox signals with a similar level of the molecular target in the sample and the standard.

24. The method of claim 23, wherein the standard contains no molecular target and comparing the first redox signal to the second redox signal comprises correlating a similarity in the first and second redox signals with an absence of molecular target in the sample and a difference in the first and second redox signals with the presence of the molecular target in the sample.

25. The method of claim 21, wherein the molecular target is selected from the group consisting of DNA, RNA, proteins, small molecules, oligonucleotides, peptides, whole cells, saccharides, and polysaccharides.

26. The method of claim 21, wherein the redox moiety is attached to the oligonucleotide reporter at the end opposite of the electrode.

27. The method of claim 21, wherein the redox signal detectable in the second state is greater than the redox signal detectable in the first state.

28. The method of claim 27, wherein the redox moiety is capable of being closer to the electrode in the second state as compared to the first state.

29. The method of claim 27, wherein the second state includes a higher level of redox moiety dynamics which enhances electron transfer from the redox moiety to the electrode as compared to the level of redox moiety dynamics in the first state.

30. The method of claim 21, wherein the electrode is capable of inducing redox events in the redox moiety.

31. The method of claim 21, wherein the electrode is selected from the group consisting of metallic conductors, nonmetallic conductors, metallic semiconductors and nonmetallic semiconductors.

* * * * *

SEQUENCE LISTING

<160> NUMBER OF SEQ ID NOS: 14

<210> SEQ ID NO 1
<211> LENGTH: 27
<212> TYPE: DNA
<213> ORGANISM: Artificial
<220> FEATURE:
<223> OTHER INFORMATION: blocker

<400> SEQUENCE: 1
gcgaggtaaa acgacggcca gtctcgc                                            27

<210> SEQ ID NO 2
<211> LENGTH: 34
<212> TYPE: DNA
<213> ORGANISM: Artificial
<220> FEATURE:
<223> OTHER INFORMATION: sensor

<400> SEQUENCE: 2
ccctatgtat gctctttgtt gtggcgagac tggc                                    34

<210> SEQ ID NO 3
<211> LENGTH: 34
<212> TYPE: DNA
<213> ORGANISM: Artificial
<220> FEATURE:
<223> OTHER INFORMATION: target

<400> SEQUENCE: 3
gccagtctcg ccacaacaaa gagcatacat aggg                                    34

<210> SEQ ID NO 4
<211> LENGTH: 38
<212> TYPE: DNA
<213> ORGANISM: Artificial
<220> FEATURE:
<223> OTHER INFORMATION: sensor

<400> SEQUENCE: 4
gcgagttaga ccgatccccc cccttcgtcc agtctttt                                38

<210> SEQ ID NO 5
<211> LENGTH: 31
<212> TYPE: DNA
<213> ORGANISM: Artificial
<220> FEATURE:
<223> OTHER INFORMATION: blocker

<400> SEQUENCE: 5
gactggacgc cccccatcg gtctaactcg c                                        31

<210> SEQ ID NO 6
<211> LENGTH: 15
<212> TYPE: DNA
<213> ORGANISM: Artificial
<220> FEATURE:
<223> OTHER INFORMATION: target

<400> SEQUENCE: 6
aaaagactgg acgaa                                                         15

<210> SEQ ID NO 7
<211> LENGTH: 27

```
<212> TYPE: DNA
<213> ORGANISM: Artificial
<220> FEATURE:
<223> OTHER INFORMATION: sensor

<400> SEQUENCE: 7
ccatctccac ttggttggtg tggttgg                                              27

<210> SEQ ID NO 8
<211> LENGTH: 21
<212> TYPE: DNA
<213> ORGANISM: Artificial
<220> FEATURE:
<223> OTHER INFORMATION: blocker

<400> SEQUENCE: 8 ccaacttttta agtggagatg g                                                   21

<210> SEQ ID NO 9
<211> LENGTH: 27
<212> TYPE: DNA
<213> ORGANISM: Artificial
<220> FEATURE:
<223> OTHER INFORMATION: control sensor

<400> SEQUENCE: 9
ccatctccac ttggtggtgg ttgtggt                                              27

<210> SEQ ID NO 10
<211> LENGTH: 21
<212> TYPE: DNA
<213> ORGANISM: Artificial
<220> FEATURE:
<223> OTHER INFORMATION: control blocker

<400> SEQUENCE: 10
accactttta agtggagatg g                                                    21

<210> SEQ ID NO 11
<211> LENGTH: 36
<212> TYPE: DNA
<213> ORGANISM: Artificial
<220> FEATURE:
<223> OTHER INFORMATION: sensor

<400> SEQUENCE: 11
tttcatctct tctccgagcc ggtcgaaata gtgagt                                    36

<210> SEQ ID NO 12
<211> LENGTH: 36
<212> TYPE: DNA
<213> ORGANISM: Artificial
<220> FEATURE:
<223> OTHER INFORMATION: sensor

<400> SEQUENCE: 12
tttcatctct tccccgagcc ggtcgaaata gtgagt                                    36

<210> SEQ ID NO 13
<211> LENGTH: 20
<212> TYPE: DNA
<213> ORGANISM: Artificial
<220> FEATURE:
<223> OTHER INFORMATION: blocker
<220> FEATURE:
<221> NAME/KEY: misc_feature
<222> LOCATION: (10)..(10)
```

```
<223> OTHER INFORMATION: ribonucleotide

<400> SEQUENCE: 13
actcactata ggaagagatg                                                   20

<210> SEQ ID NO 14
<211> LENGTH: 20
<212> TYPE: DNA
<213> ORGANISM: Artificial
<220> FEATURE:
<223> OTHER INFORMATION: blocker

<400> SEQUENCE: 14
actcactata ggaagagatg                                                   20
```